US011890388B2

(12) United States Patent
Anraku et al.

(10) Patent No.: US 11,890,388 B2
(45) Date of Patent: Feb. 6, 2024

(54) STERILIZATION METHOD AND STERILIZATION DEVICE

(71) Applicant: Saraya Co., Ltd., Osaka (JP)

(72) Inventors: Daiki Anraku, Osaka (JP); Tomomasa Itarashiki, Osaka (JP); Haijun Zhang, Shandong (CN); Guoqiang Qu, Shandong (CN); Min Yang, Shandong (CN)

(73) Assignee: SARAYA CO., LTD., Osaka (JP)

( * ) Notice: Subject to any disclaimer, the term of this patent is extended or adjusted under 35 U.S.C. 154(b) by 535 days.

(21) Appl. No.: 16/603,919

(22) PCT Filed: Apr. 10, 2018

(86) PCT No.: PCT/JP2018/014990
§ 371 (c)(1),
(2) Date: Oct. 9, 2019

(87) PCT Pub. No.: WO2018/190317
PCT Pub. Date: Oct. 18, 2018

(65) Prior Publication Data
US 2020/0121817 A1 Apr. 23, 2020

(30) Foreign Application Priority Data
Apr. 10, 2017 (CN) .......................... 201710230693.7

(51) Int. Cl.
*A61L 2/20* (2006.01)
*A61L 2/26* (2006.01)

(52) U.S. Cl.
CPC ................... *A61L 2/20* (2013.01); *A61L 2/26* (2013.01); *A61L 2202/11* (2013.01);
(Continued)

(58) Field of Classification Search
CPC ... A61L 2202/11; A61L 2/20; A61L 2202/122
See application file for complete search history.

(56) References Cited

U.S. PATENT DOCUMENTS

| 5,084,239 A | 1/1992 | Moulton et al. |
| 5,244,629 A | 9/1993 | Caputo et al. |

(Continued)

FOREIGN PATENT DOCUMENTS

| EP | 0336047 A1 | 10/1989 |
| EP | 2 554 514 A1 | 2/2013 |

(Continued)

OTHER PUBLICATIONS

"Baffle Thickness, 2007-2013, Science Direct" (Year: 2007).*

(Continued)

*Primary Examiner* — Kevin Joyner
(74) *Attorney, Agent, or Firm* — BUCHANAN INGERSOLL & ROONEY PC

(57) ABSTRACT

A sterilization apparatus includes a sterilization chamber, a vaporization chamber, a wall partitioning the vaporization chamber into a first chamber and a second chamber, a first passage connecting the first chamber and the second chamber, a table arranged in the first chamber, a nozzle arranged toward the table to spray a sterilizing agent toward the table, a liquid reservoir for storing the liquid component of the sterilizing agent sprayed toward the table, a second passage connecting the second chamber and the sterilization chamber, and a means for decompressing the sterilization chamber and also decompressing the first chamber and the second chamber of the vaporization chamber through the first passage and the second passage, wherein the first passage is formed by a belt-shaped gap having a small thickness and a large width.

10 Claims, 10 Drawing Sheets

(52) U.S. Cl.
CPC ... *A61L 2202/122* (2013.01); *A61L 2202/123* (2013.01); *A61L 2202/15* (2013.01); *A61L 2202/24* (2013.01)

(56) References Cited

U.S. PATENT DOCUMENTS

| | | | |
|---|---|---|---|
| 6,365,102 | B1 | 4/2002 | Wu et al. |
| 7,713,473 | B2 | 5/2010 | Kendall et al. |
| 8,658,092 | B2 | 2/2014 | Kohler et al. |
| 2004/0182855 | A1 | 9/2004 | Centanni |
| 2017/0225094 | A1* | 8/2017 | Ju ............... B01D 1/20 |

FOREIGN PATENT DOCUMENTS

| | | |
|---|---|---|
| JP | 2780228 B2 | 7/1998 |
| JP | 2005-087353 A | 4/2005 |
| JP | 2007-007422 A | 1/2007 |
| JP | 4526649 B2 | 8/2010 |
| RU | 2392970 C2 | 6/2010 |
| WO | 2006/101467 A1 | 9/2006 |
| WO | 2007/014435 A1 | 2/2007 |
| WO | 2014/202393 A1 | 12/2014 |

OTHER PUBLICATIONS

Office Action dated Feb. 11, 2021, by the Russian Patent Office in corresponding Russian Patent Application No. 2019131573, and an English Translation of the Office Action. (14 pages).

European Search Report issued in corresponding European Patent Application No. 18784709.0, dated Dec. 7, 2020 (8 pages).

International Search Report (PCT/ISA/210) dated May 29, 2018, by the Japanese Patent Office as the International Searching Authority for International Application No. PCT/JP2018/014990.

Written Opinion (PCT/ISA/237) dated May 29, 2018, by the Japanese Patent Office as the International Searching Authority for International Application No. PCT/JP2018/014990.

* cited by examiner

STERILIZATION METHOD AND STERILIZATION DEVICE

TECHNICAL FIELD

The present invention relates to a sterilization method and a sterilization device.

BACKGROUND ART

A dry heat sterilization method and a high-pressure steam sterilization method have been conventionally employed for sterilization process of medical equipment. In these sterilization methods, medical devices are subjected to heating process in a relatively high temperature environment. However, due to diversification of medical devices, an increasing number of medical devices are partially made of materials unable to withstand high temperature, and a new sterilization method is required for such medical devices. Additionally, a medical device having a long thin hollow tube such as an endoscope must be subjected to sterilization process completely to the end of the hollow tube.

In a method proposed as a sterilization method capable of satisfying such requirements, a sterilization gas is generated by injecting an agent for sterilization process into a reduced-pressure environment to sterilize a sterilization object under the reduced-pressure environment with the sterilization gas, and this sterilization method can provide sterilization process throughout the thin hollow tube without using high temperature.

However, while hydrogen peroxide is generally used as a sterilant in this sterilization method, it may be difficult to perform sufficient sterilization with hydrogen peroxide alone for the sterilization of medical devices requiring an advanced sterilization process. Therefore, it is also known that a peracid agent containing peracetic acid as a sterilant provides providing a high sterilization effect even in a relatively small amount.

PRIOR ART DOCUMENT

Patent Document

Patent Document 1: Japanese Patent No. 2780228
Patent Document 2: Japanese Patent No. 4526649

If, however, hydrogen peroxide or peracetic acid is supplied to a sterilization chamber directly in a liquid state, this will lead to corrosion of members constituting the sterilization chamber. Therefore, when this type of sterilant is supplied to the sterilization chamber, a negative pressure is introduced into the sterilization chamber, and the sterilant is then sprayed into the sterilization chamber under the negative pressure. However, if a large amount of the sterilant is injected into the sterilization chamber at one time, the sterilant is not completely vaporized so that some non-vaporized sterilant remains in the sterilization chamber and may cause corrosion.

SUMMARY OF THE INVENTION

Problem to be Solved by the Invention

An object of the present invention is to eliminate the problem of corrosion described above.

Means for Solving Problem

To achieve this object,
an embodiment of a sterilization device according to the present invention comprises
a sterilization chamber;
a vaporization chamber;
a wall partitioning the vaporization chamber into a first room and a second room;
a first passage connecting the first room and the second room;
a table disposed in the first room;
a nozzle disposed toward the table and spraying a sterilant toward the table;
a liquid reservoir part accumulating a liquid component of the sterilant sprayed toward the table;
a second passage connecting the second room and the sterilization chamber; and
a means depressurizing the sterilization chamber and depressurizing the first room and the second room of the vaporization chamber through the first passage and the second passage, and
the first passage is made up of a belt-shaped gap having a small thickness and a wide width.

In the sterilization device according to another embodiment of the present invention,
the wall includes a partition wall rising from a bottom of the vaporization chamber, and
the sterilization device includes a belt-shaped gap formed between an upper end surface of the partition wall and a ceiling surface of the vaporization chamber.

In the sterilization device according to another embodiment of the present invention,
the wall includes a first wall rising from a bottom of the vaporization chamber and a second wall hanging down from a ceiling of the vaporization chamber, and
the belt-shaped gap is formed between the first wall and the second wall.

In a sterilization device according to another embodiment of the present invention,
a tray is disposed below an end portion of the second passage connected to the sterilization chamber.

According to the sterilization device of the embodiments of the present invention, the sterilization gas moving from the first room to the second room comes into contact with the belt-shaped wall. Therefore, liquid components (particularly, phosphoric acid and sulfuric acid having high boiling points) contained in the sterilization gas are captured by the contact with the wall and are not carried to the sterilization chamber.

MODES FOR CARRYING OUT THE INVENTION

1. Configuration of Sterilization Device

Figure 1:
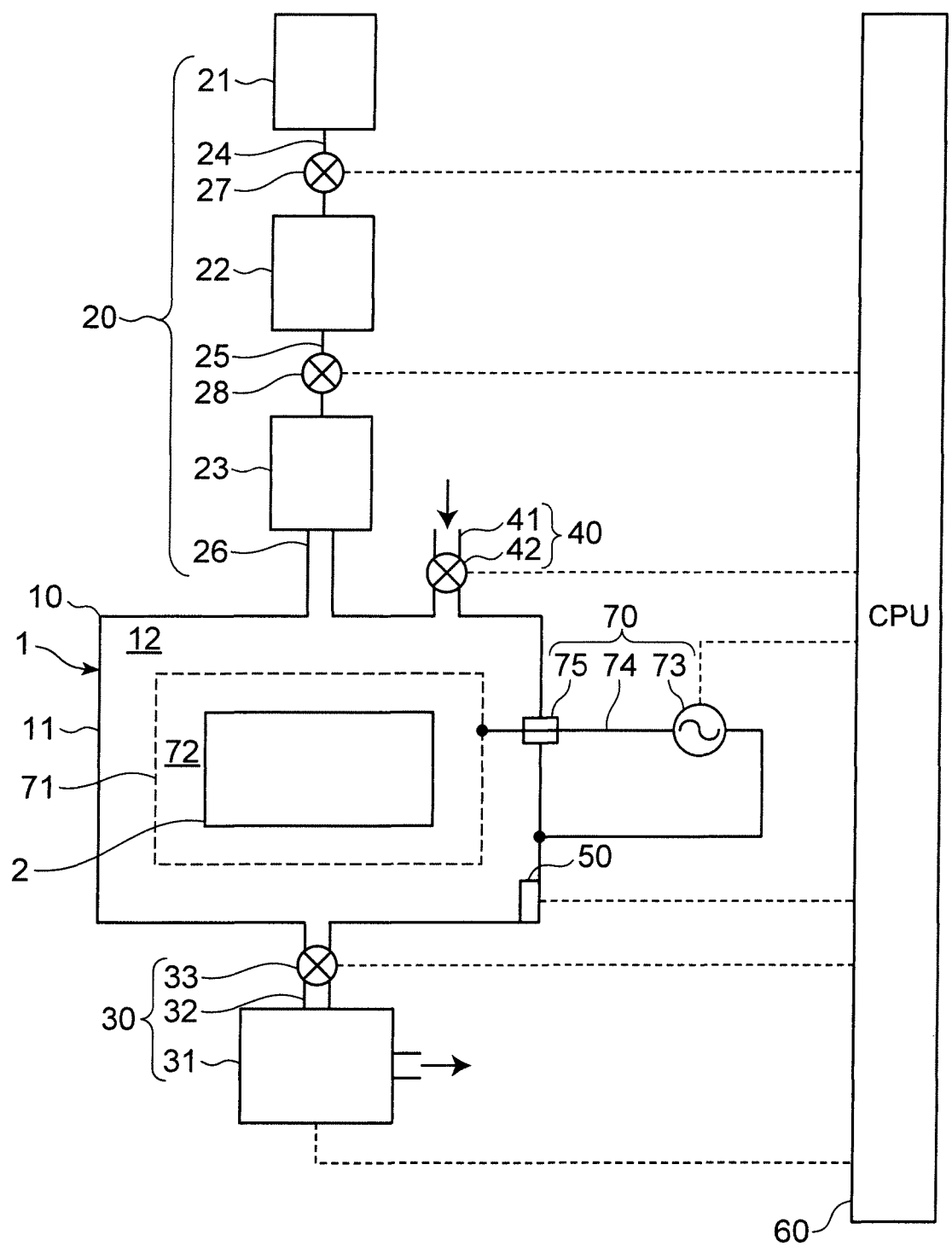
FIG. 1 is a diagram showing a schematic configuration of a sterilization device according to the present invention.

FIG. 1 schematically shows an overall configuration of a sterilization device according to an embodiment of the present invention. As shown in FIG. 1, the sterilization device 1 has a housing 10 for forming a sterilization chamber described later. The housing 10 has an outer container 11.

The outer container 11, which is formed by processing a plate of conductive metal (e.g., aluminum), for example, includes a chamber (hereinafter referred to as "sterilization chamber") 12 sealed therein. Although not shown, the outer container 11 includes a container main body and a lid for introducing a sterilization object 2 into and taking the object out of the sterilization chamber 12.

The sterilization container 10 is coupled to a sterilization gas supply device (supplying means) 20 supplying a sterilization gas to the sterilization chamber 12, a vacuum device (depressurizing means) 30 introducing a vacuum into the sterilization chamber 12, and a ventilation device 40 replacing the sterilization gas in the sterilization chamber 12 with atmospheric air.

The sterilization gas supply device 20 has a storage unit 21 storing a liquid sterilant, a measurement unit (measurement chamber) 22 for measuring the sterilant supplied from the storage unit 21, a vaporization unit (vaporization chamber) 23 for vaporizing a predetermined amount of the sterilant measured by the measurement unit 22, a passage (sterilant supply passage) 24 connecting the storage unit 21 and the measurement unit 22, a passage (sterilant supply passage) 25 connecting the measurement unit 22 and the vaporization unit 23, a passage (sterilization gas supply passage) 26 connecting the vaporization unit 23 and the sterilization chamber 12, a valve 27 disposed in the passage 24 to open and close the passage 24, and a valve 28 provided in the passage 25 to open and close the passage 25. The configuration of the sterilization gas supply device 20 will be described later. Various liquid sterilants can be used as the sterilant and, for example, hydrogen peroxide and peracetic acid are suitable. As is well known, peracetic acid often exists in the form of an equilibrium mixture of peracetic acid, acetic acid, hydrogen peroxide, and water.

The vacuum device 30 includes a vacuum pump 31, a passage (exhaust passage) 32 connecting the vacuum pump 31 and the sterilization chamber 12, and a valve 33 provided in the passage 31 to open and close the passage 31.

The ventilation device 40 includes a passage (ventilation passage) 41 connecting the sterilization chamber 12 to the atmosphere, and a valve 42 provided in the passage 41 to open and close the passage 41.

A pressure detector 50 for detecting a pressure in the sterilization chamber 12 is disposed inside the outer container 11. The pressure detector 50 may be made up of one or more pressure gauges. When multiple pressure gauges are used, for example, a range from atmospheric pressure to 10,000 pascals is measured with one pressure gauge, and a range from 13,000 pascals to 0 pascals is measured with another pressure gauge.

The measurement unit 22, the valves 27, 28, the vacuum pump 31, the valve 33, the valve 42, and the pressure detector 50 are connected to a control device 60.

In addition to the configuration described above, the embodiment is provided with a plasma generation device 70 generating plasma in the sterilization chamber 12. The plasma generating device 70 has an inner container 71 disposed inside the outer container 11. For example, the inner container 71 is formed by processing a porous plate (e.g., punching metal) of conductive metal (e.g., aluminum) to form a room 72 (a portion of the sterilization chamber 12) in which the sterilization object 2 is placed. Although not shown, the inner container 71 includes a container main body and a lid for putting the sterilization object 2 into and out from the room 72. Although not shown, a spacer made of an electrically insulating material is disposed between the outer container 11 and the inner container 71, and the outer container 11 and the inner container 71 are thereby electrically insulated. The inner container 71 is electrically connected to the outer container 11 via a circuit 74 having a high frequency power source 73. The high frequency power source 73 is connected to the control device 60. An insulating sleeve 75 is disposed at a position where the circuit 74 penetrates the outer container 11, and the circuit 74 and the outer container 11 are thereby electrically insulated.

2. Operation of Sterilization Device

A sterilization process performed by the sterilization device 1 will be described with reference to FIGS. 2 to 5. The sterilization process described below has a preparation process, a first sterilization process, a second sterilization process, a sterilization gas decomposition process, and a ventilation process.

(1) Preparation Process

In the preparation process, the lid of the outer container 11 and the lid of the inner container 71 are opened, and the sterilization object 2 is placed in the room 72 of the inner container 71. The sterilization object 2 is a medical device such as an endoscope or an elongated tube for an endoscope, for example. When the sterilization object 2 is placed, the lid of the inner container 71 and the lid of the outer container 11 are closed, and the sterilization chamber 12 is sealed.

(2) First Sterilization Process 101

When the preparation process is completed and the sterilization device 1 is activated, the control device 60 executes steps described below.

Step #1:

The control device 60 closes the valves 27, 28, 33, 42 of the sterilization gas supply device 20, the vacuum device 30, and the ventilation device 40 and turns off the high-frequency power source 73 of the plasma generation device 70. The control device 60 initializes data stored in a storage unit (not shown) of the control device 60 (step #1). Specifically, t1 to t3 and n1 to n4 described later are reset to "0", and N1 to N3 are set to "2", "6", "10", respectively.

Step #2:

The control device 60 drives the vacuum pump 31 of the vacuum device 30 and opens the valve 33 to depressurize the sterilization chamber 12 (step #2). As a result, the pressure in the sterilization chamber 12 gradually decreases from the atmospheric pressure.

Step #3:

During depressurization, the control device 60 determines whether a pressure P in the sterilization chamber 12 has reached a predetermined pressure P1 (e.g., 120 pascals) based on an output of the pressure detector 50 (step #3).

Step #4:

When it is detected that the pressure P in the sterilization chamber 12 has reached the pressure P1, the control device 60 turns on the high-frequency power source 73 of the plasma generation device 70 (step #4). As a result, plasma is generated between the outer container 11 and the inner container 71, and the atmosphere of the sterilization chamber 12 is warmed to an appropriate temperature.

Steps #5, #6:

Using the output of the pressure detector 50, the control device 60 determines whether the pressure P in the sterilization chamber 12 has reached a predetermined pressure 92 (e.g., 65 pascals) (step #5), and when the pressure in the sterilization chamber 12 has reached the predetermined pressure P2, the control device 60 closes the valve 33 of the vacuum device 30 (step #6). Actually, the pressure may slightly increase after the valve 33 is closed, and therefore, the control device 60 preferably maintains the pressure in the sterilization chamber 12 at a predetermined pressure P2 while opening and closing the valve 33. Since the sterilization chamber 12 and the vaporization unit 23 communicate with each other via the passage 26 as described above, the negative pressure introduced into the sterilization chamber 12 is also introduced into the vaporization unit 23, and the pressure of the vaporization unit 23 is also set to the predetermined pressure 92.

Steps #7, #8:

The control device 60 starts a timer t1 (step #7). The control device 60 then determines whether a value of a counter n1 counting the number of times of sterilization is equal to a predetermined value N1 (=2) (step #8). In this embodiment, since the sterilization object is sterilized through two sterilization processes, i.e., the first sterilization process and the second sterilization process, N1 is set to "2" as described above. On the other hand, the counter n1 is set to "0" at the initialization step #1, and "1" is added every time one sterilization process is completed (step #25 described later). Therefore, n1 is set to "0" during the first sterilization process, n1 is set to "1" during the second sterilization process, and n1 is set to "2" when the second sterilization process is completed. Therefore, the control device 60 performs steps #9A to #10A during the first sterilization process and the second sterilization process, and the control device 60 performs steps #9B to #10B after the second sterilization process is completed.

Step #9A, 10A:

The control device 60 determines whether the count time of the timer t1 has reached T1 (e.g., 1 minute) (step #9A) and, when the count time of the timer t1 has reached T1, the control device 60 turns off the high frequency power source 73 (step 10A) to stop the generation of plasma.

Step #11:

The control device 60 measures the sterilant supplied from the sterilant storage unit 21 with the measurement unit (measuring chamber) 22 to prepare a predetermined amount (e.g., 1 milliliter) of the sterilant. Specifically, the control device 60 opens the closed valve 28 to depressurize the measurement unit 22 and closes the valve 28 after elapse of a predetermined time so as to keep the measurement unit 22 in a negative pressure environment. Subsequently, the control device 60 opens the valve 27. As a result, the predetermined amount (e.g., 1 milliliter) of the sterilant is supplied from the storage unit 21 to the measurement unit 22. When the supply of the sterilant is completed, the control device 60 closes the valve 27.

Step #12:

The control device 60 opens the valve 28 of the sterilization gas supply device 20. When the valve 28 is opened, the predetermined amount (1 milliliter) of the sterilant prepared in the measurement unit 22 is sprayed into the vaporization unit 23 since the vaporization unit 23 is set to a negative pressure (e.g., 65 pascals) and the total volume of the vaporization unit 23 and the sterilization chamber 12 is much larger than the volume of the measurement unit 22. As is well known, the boiling point of the sterilant is low under a negative pressure, and therefore, the sprayed sterilant is instantly vaporized into a sterilization gas.

Step #13:

When one spray is completed, the control device 60 adds "1" to a counter n2 of the number of sprays (step #13). The number counter n2 is set to "0" at the initialization step #1.

Steps #14 to #15:

The control device 60 starts a timer t2 (step #14) and determines whether the count time of the timer t2 has reached T2 (e.g., 80 seconds) (step #15), and when the count time of the timer t2 has reached T2, the control device 60 closes the valve 28 (step #16). As described above, the negative pressure is introduced into the measurement unit 22 by opening the valve 28. Therefore, when the valve 27 is opened later, a predetermined amount of the sterilant is sucked from the storage unit 21 into the measurement unit 22.

Figure 2:
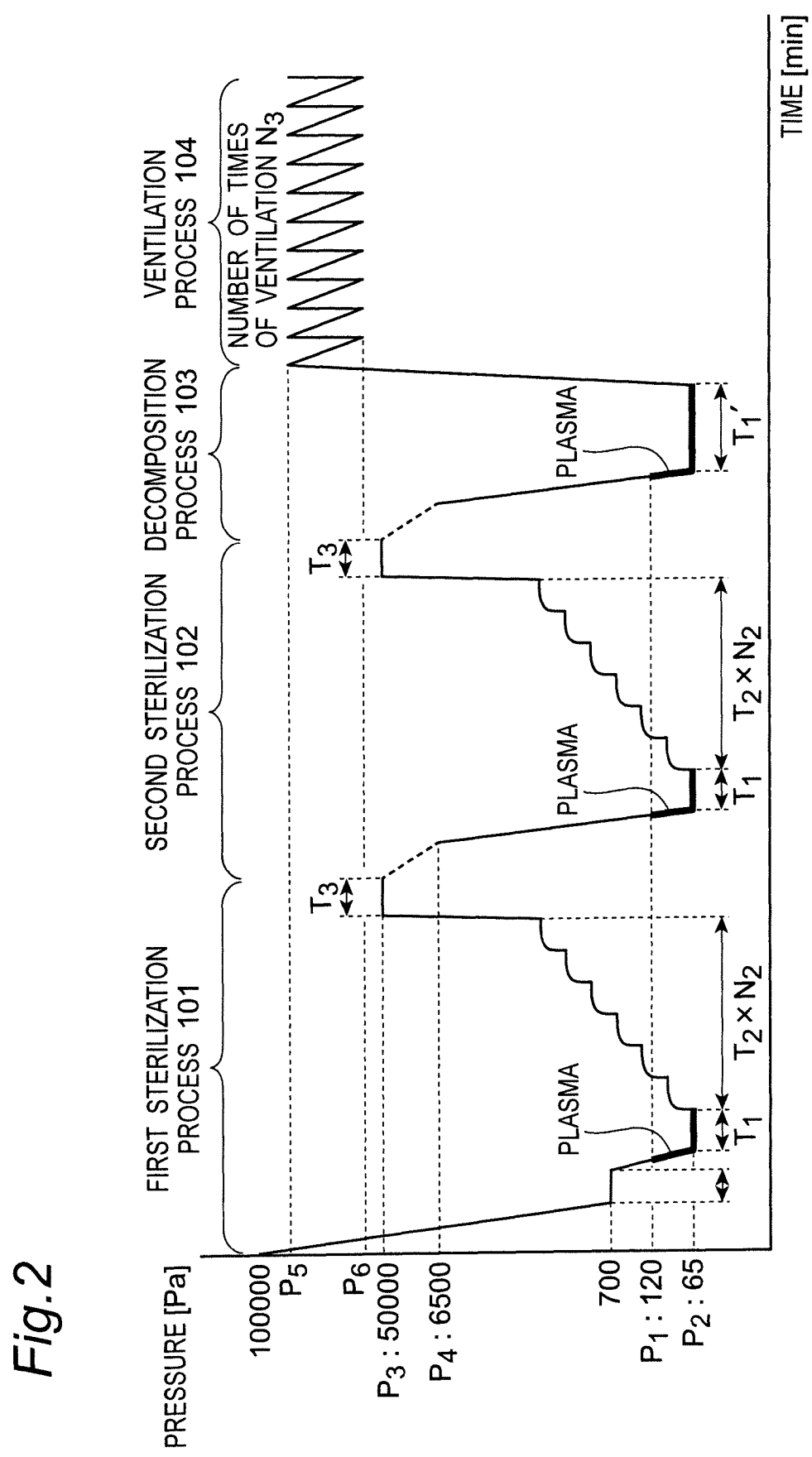
FIG. 2 is a diagram showing a relationship between pressure and time of a sterilization chamber for describing an operation of the sterilization device shown in FIG. 1.
Figure 3:
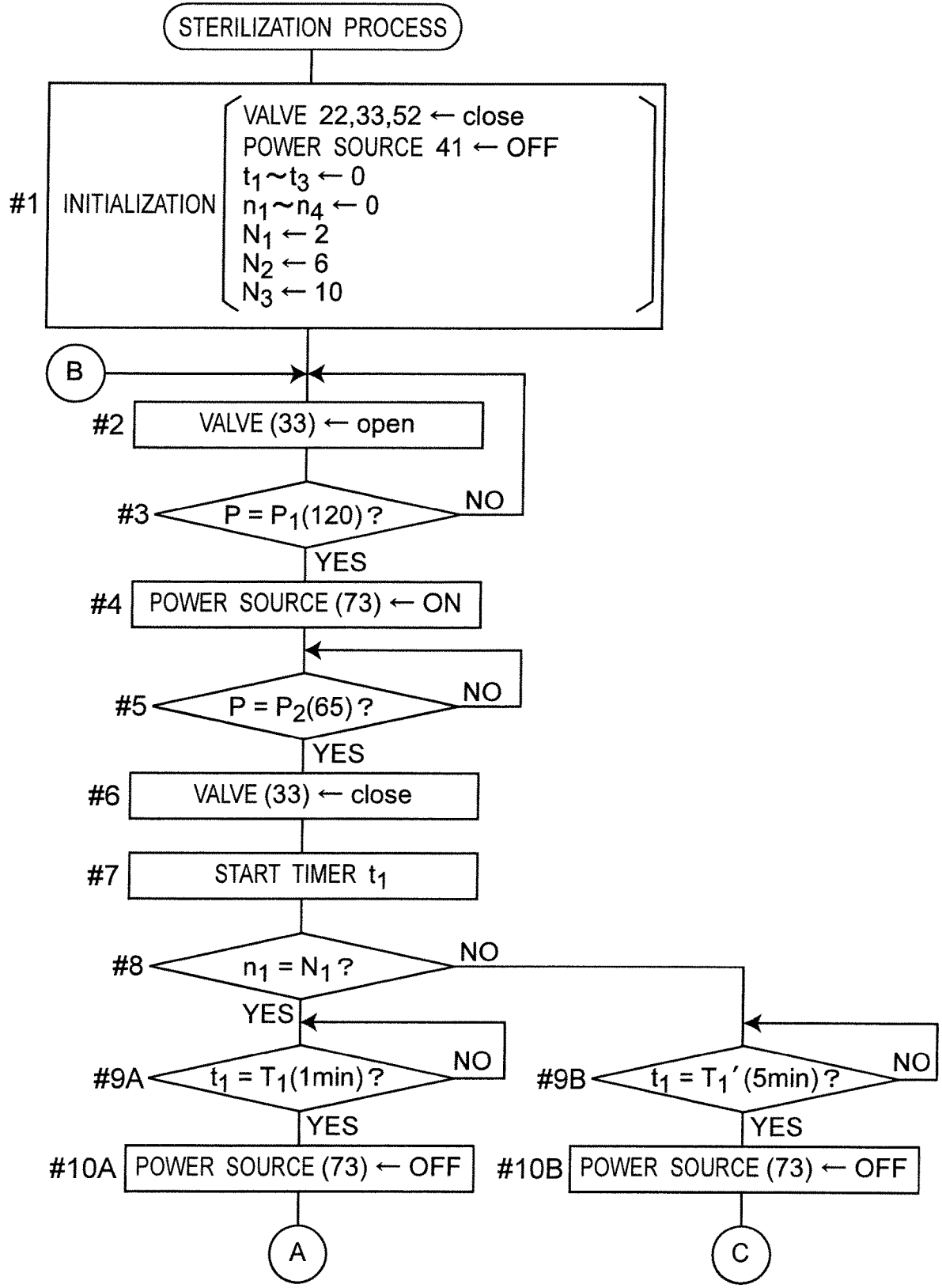
FIG. 3 is a flowchart for describing an operation of sterilization process shown in FIG. 1.
Figure 4:
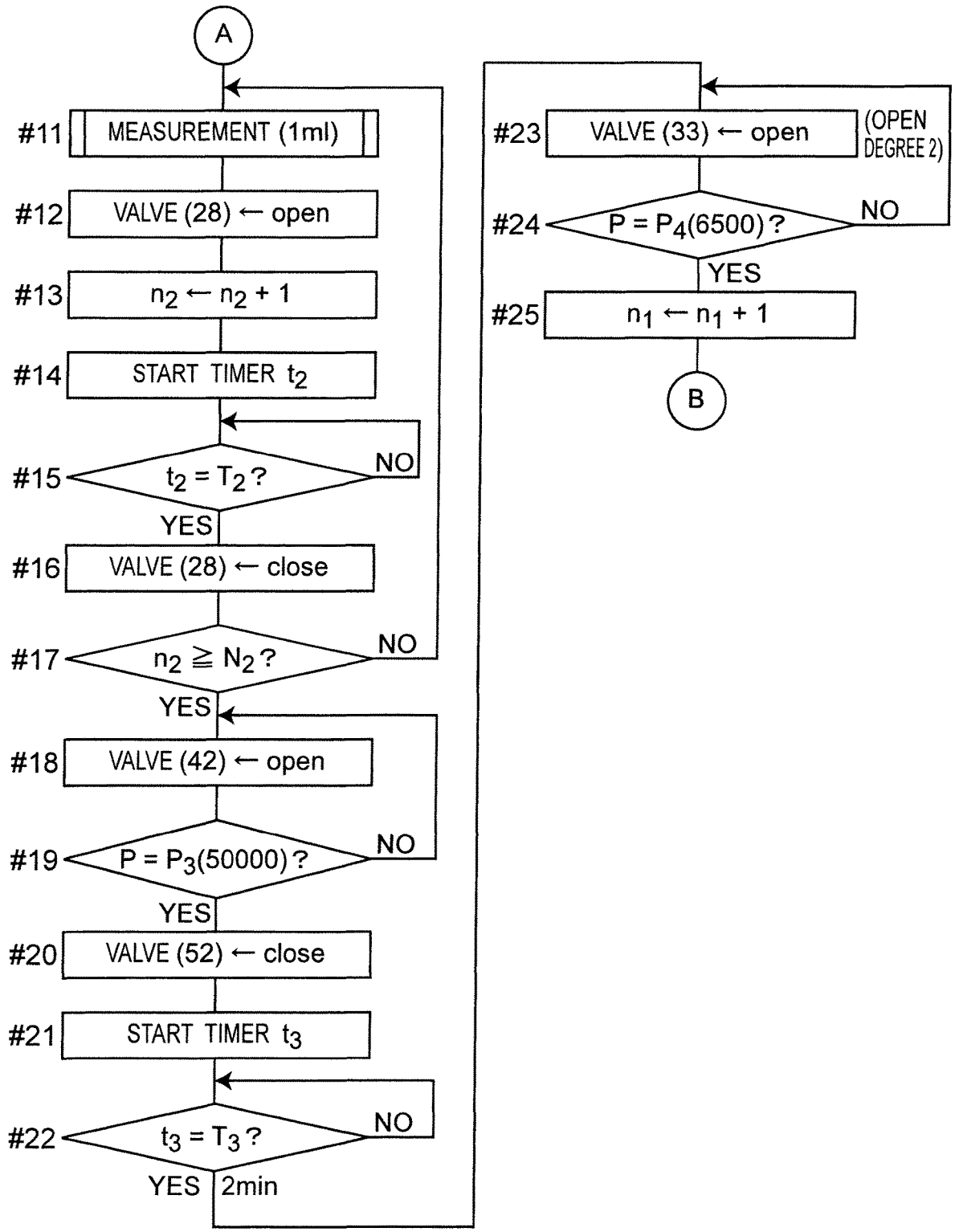
FIG. 4 is a flowchart for describing the operation of sterilization process shown in FIG. 1.
Figure 5:
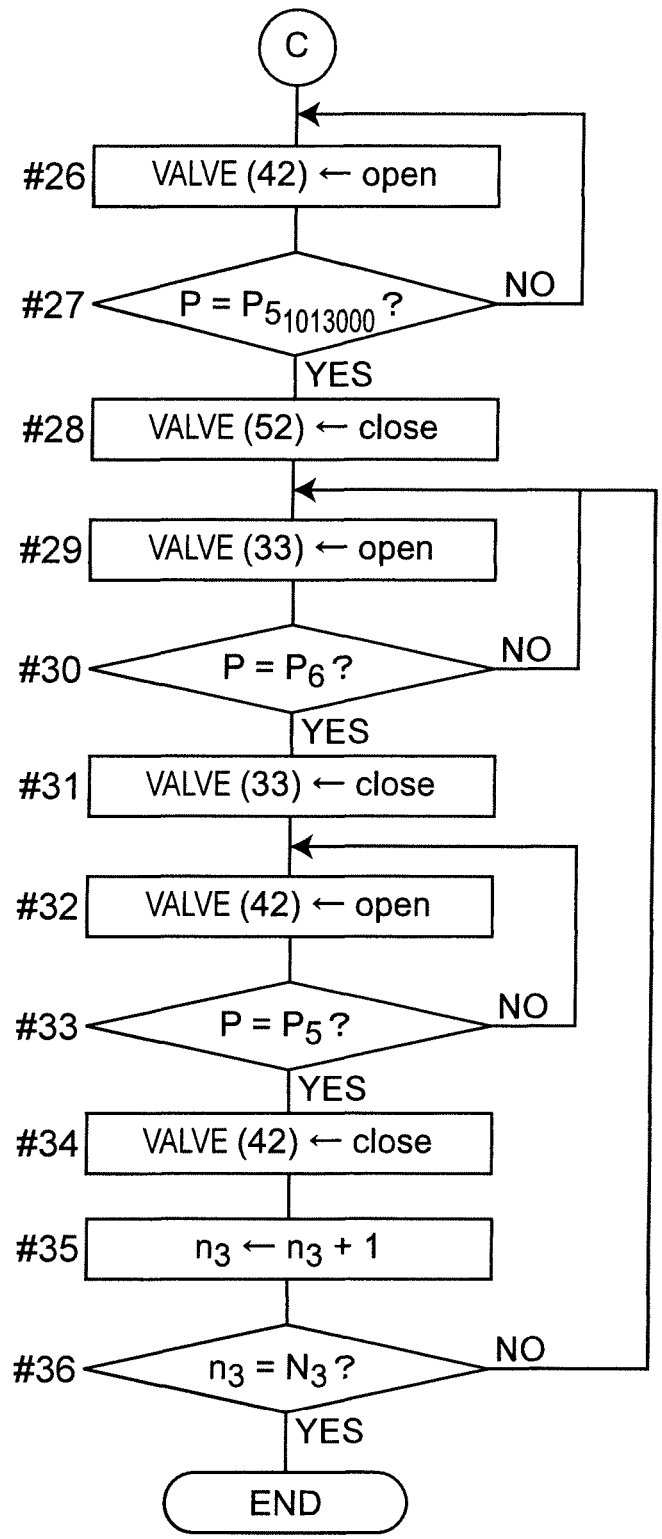
FIG. 5 is a flowchart for describing the operation of sterilization process shown in FIG. 1.

Step #17:

The control device 60 determines whether the value of the counter n2 of the number of sprays has reached N2 (step #17), and if n2 is less than N2, the control device 60 performs steps #11 to #16. For example, in the embodiment, N2 is set to "6" in the initialization step #1. Therefore, as shown in FIG. 2, the measurement, spraying, and vaporization of a small amount (e.g., 1 milliliter) of the sterilant are repeated multiple times, and the pressure in the sterilization chamber 12 increases stepwise and sequentially in the embodiment. As a result, even a medical device such as an elongated tube is sterilized to the end with the sterilization gas repeatedly entering a narrow internal space thereof.

Preferably, after the sterilant for spraying is introduced n2-times into the vaporization unit 23, the valve 28 is closed; the valve 27 is opened with the measurement unit 2 kept in a depressurized state so that a residual sterilant in the passage 24 is introduced into the measurement unit 22; and the valve 28 is opened again to introduce the residual sterilant into the vaporization unit 23. As a result, the passage 24 can be emptied and returned to an initial state.

Steps #18 to #19:

When the repeated sterilization process described above is completed, the control device 60 opens the valve 42 of the ventilation device 40 to introduce the atmospheric air into the sterilization chamber 12. The control device 60 determines whether the pressure P in the sterilization chamber 12 has reached a predetermined pressure P3 (e.g., 50,000 pascals) based on the output of the pressure detector 50 (step #19). When the pressure P in the sterilization chamber 12 has reached P3, the control device 60 closes the valve 42 (step #20).

Steps #21 to #22:

The control device 60 starts a timer t3 (step #21) and waits until the count time of the timer t3 reaches T3 (e.g., 2 minutes) (step #22).

The first sterilization process 101 is complete as described above.

(2) Second Sterilization Process 102
Steps #23 to #24:

When entering the second sterilization process 102 (see FIG. 2), the control device 60 drives the vacuum pump 31 of the vacuum device 30 and opens the valve 33 to depressurize the sterilization chamber 12 (step #23). Subsequently, the control device 60 determines whether the pressure P in the sterilization chamber 12 has reached a predetermined pressure P4 (e.g., 6,500 pascals) based on the output of the pressure detector 50 (step #24). In the embodiment, a depressurization rate (=pressure reduction amount/time) in this case is set smaller than the depressurization rate of steps #2 to #3 described above. However, the depressurization rate of steps #23 to #24 may be the same as the depressurization rate of steps #2 to #3. The depressurization rate can be adjusted by adjusting an opening degree of the valve 33, for example.

Step #25:

When the pressure in the sterilization chamber 12 has reached P4, the control device 60 adds "1" to the counter n1 (step #25). Therefore, the counter n1 set to "0" at the initialization step #1 is updated to "1" at this step.

Steps #2 to #22:

Subsequently, the control device 60 returns to step #2 and performs steps #2 to #22 described above. In this case, the counter n1 is "1" as described above, and therefore, it is determined that n10N1 is satisfied at step #8 during the second sterilization process, and steps 9A to 10A are performed.

The second sterilization process 102 is completed as described above.

(3) Decomposition Process 103

When entering the decomposition process 103 (see FIG. 2), the control device 60 drives the vacuum pump 31 of the vacuum device 30 and opens the valve 33 to depressurize the sterilization chamber 12 (step #23). Subsequently, the control device 60 determines whether the pressure P in the sterilization chamber 12 has reached a predetermined pressure P4 (e.g., 6,500 pascals) based on the output of the pressure detector 50 (step #24). In the embodiment, the depressurization rate (=pressure reduction amount/time) in this case is set smaller than the depressurization rate of steps #2 to #3 described above. However, the depressurization rate of steps #23 to #24 may be the same as the depressurization rate of steps #2 to #3.

Step #25:

When the pressure in the sterilization chamber 12 has reached P4, the control device 60 adds "1" to the counter n1 (step #25). Therefore, the counter n1 set to "1" after the completion of the first sterilization process is reset to "2" at this step.

Steps #2 to #7:

Subsequently, the control device 60 returns to step #2 and performs steps #2 to #7 described above.

Step #8:

Subsequently, at step #8, the control device 60 determines whether the counter n1 is equal to N1. As described above, the counter n1 is set to "2" at this point. Therefore, the control device 60 determines that n1=N1 is satisfied and performs steps 9B to 10B. Specifically, at step 9B, it is determined whether the count time of the timer t1 has reached T1' (e.g., 5 minutes) (step #9B), and when the count time of the timer t1 has reached T1', the high frequency power source 73 turned on at step #4 is turned off (step 105) and the generation of plasma is stopped.

As described above, at the decomposition process 103, plasma is generated for a long time (e.g., 5 minutes). Consequently, the sterilant (e.g., hydrogen peroxide, peracetic acid) adhering to an inner surface of the sterilization chamber 12, the inner container 71, and the sterilization object 2 is decomposed into water and carbon dioxide and is made odorless.

Step #26:

Subsequently, the control device 60 opens the valve 42 of the ventilation device 40 to introduce the atmospheric air into the sterilization chamber 12. The control device 60 determines whether the pressure P in the sterilization chamber 12 has reached a predetermined pressure P5 (e.g., the atmospheric pressure (1,013,000 pascals) or substantially the atmospheric pressure) based on the output of the pressure detector 50 (step #27). When the pressure P in the sterilization chamber 12 has reached P5, the control device 60 closes the valve 42 (step #28).

The decomposition process 103 is completed as described above.

(4) Ventilation Process 104

When entering the ventilation process 104 (see FIG. 2), the control device 60 drives the vacuum pump 31 of the vacuum device 30 and opens the valve 33 to depressurize the sterilization chamber 12 (step #29). Subsequently, the control device 60 determines whether the pressure P in the sterilization chamber 12 has reached a predetermined pressure P6 (e.g., 30,000 pascals) based on the output of the pressure detector 50 (step #30).

Step #31:

When the pressure in the sterilization chamber 12 has reached P6, the control device 60 closes the valve 33 (step #31).

Steps #32 to #34:

Subsequently, the control device 60 opens the valve 42 of the ventilation device 40 to introduce the atmospheric air into the sterilization chamber 12. The control device 60 determines whether the pressure P in the sterilization chamber 12 has reached the predetermined pressure P5 (e.g., the atmospheric pressure (1,013,000 pascal) or substantially the atmospheric pressure) based on the output of the pressure detector 50. (step #33). When the pressure P in the sterilization chamber 12 has reached P5, the control device 60 closes the valve 42 (step #34).

Step #35:

Subsequently, the control device 60 adds "1" to a counter n3 (step #35) and determines whether the value of the counter n3 after the addition is equal to N3, and repeats steps #29 to #36 if n3≠N3 is satisfied. The counter n3 is set to "0" at the initialization step #1, and "1" is added every time one ventilation processing (steps #29 to #34) is completed. N3 is set to "10" at the initialization step #1. Therefore, in the embodiment, the control device 60 repeats the ventilation process eight times.

As described above, in the last ventilation process 104, depressurization and pressurization are repeated multiple times, and consequently, the atmosphere in the sterilization chamber 12 is favorably replaced.

3. Sterilization Gas Supply Device

Figure 6:
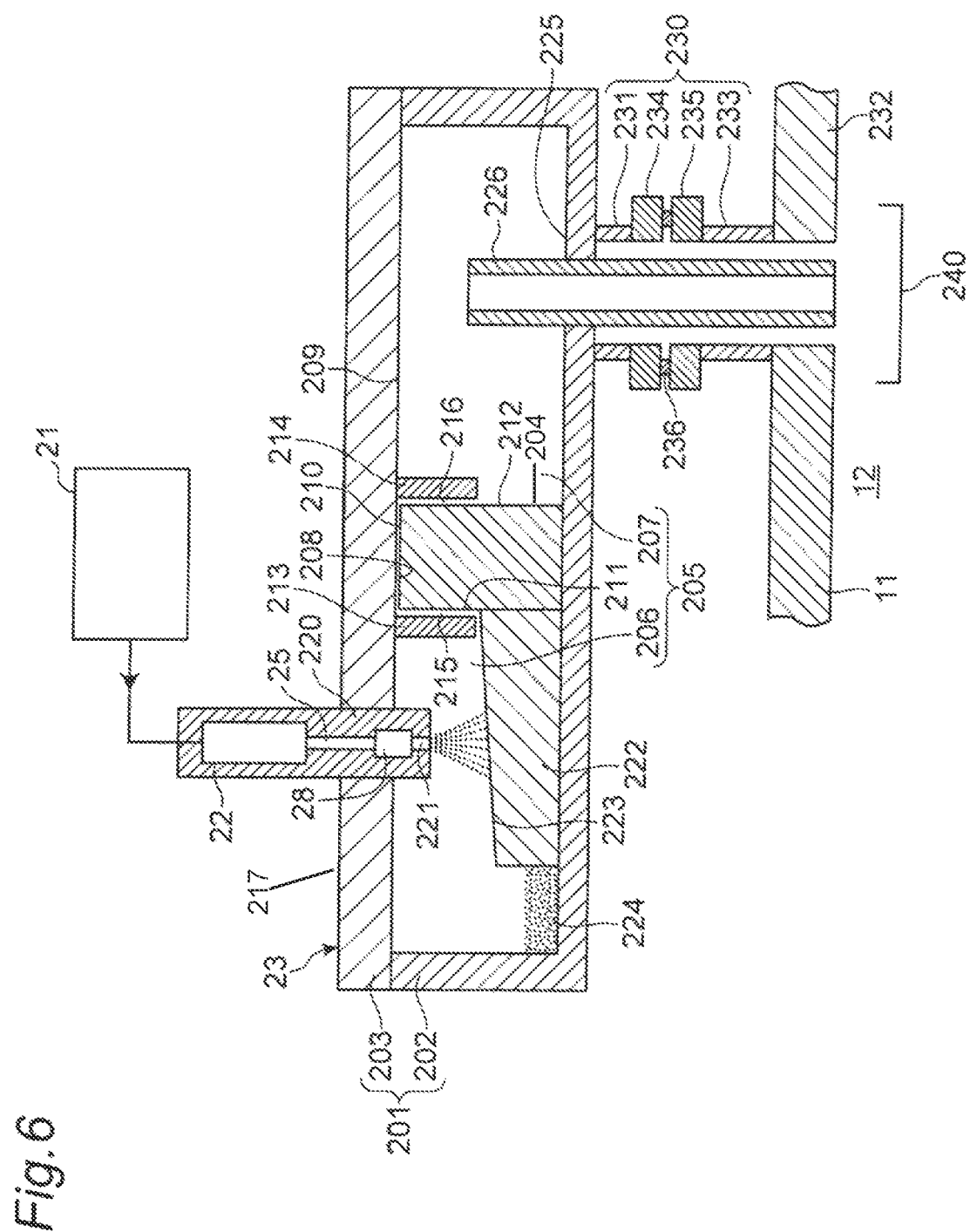
FIG. 6 is a diagram showing a configuration of a vaporization unit shown in FIG. 1

FIG. 6 shows the configuration of the sterilization gas supply device 20. As described above, the sterilization gas supply device 20 includes the storage unit 21, the measurement unit 22, and the vaporization unit 23. The vaporization unit 23 includes a container 201. The container 201 includes a container main body 202 having an upper opening and an upper lid 203 closing the upper opening of the container main body 202. The container main body 202 has a partition wall 204 extending upward from a bottom portion thereof, and an internal space (vaporization chamber) 205 of the container main body 202 is divided into two rooms (a first room 206 and a second room 207). The height of the partition wall 204 is determined such that a gap 210 of about 1 mm is formed between an upper end surface 208 of the partition wall 204 and a lower surface (ceiling surface) 209 of the lid 203.

On the lower surface 209 of the lid 203, hanging walls 213, 214 are formed to extend downward from the lower surface 209 along left and right wall surfaces (a wall surface 211 in contact with the first room 206 and a wall surface 212 in contact with the second room 207) of the partition wall 204. Gaps 215, 216 of about 1 mm are respectively formed between the hanging walls 213, 214 and the wall surfaces 211, 212 of the partition wall 204 adjacent thereto.

A sterilant spray nozzle 220 is detachably coupled to a lid portion 217 adjacent to the first room 206. The nozzle 220 includes therein the sterilant supply passage 25 and the valve 28 described above and is fixed with an injection port 221 of the nozzle 220 facing downward.

A table 222 is disposed below the injection port 221 inside the first room 206. An upper surface 223 of the table 222 is sloped. A liquid reservoir part 224 is formed beside the table 222.

On the other hand, a bottom portion 225 of the container main body 202 adjacent to the second room 207 is provided with a pipe (passage) 226 penetrating the bottom portion 225. The inner diameter of the pipe 226 is considerably larger than the size of the gaps 210, 215, 216 and is about 10 mm, for example.

The pipe 226 is surrounded by a protective cylinder 230. The protective cylinder 230 is made up of a pipe 231 extending downward from the bottom portion 225 of the container main body 202, a pipe 233 extending upward from a ceiling wall 232 of the outer container 11 forming the sterilization chamber 12, flanges 234, 235 fixed to end portions of the pipes 231, 233 and coupled to each other by bolts and nuts, and a gasket 236 sealing the flanges 234, 235. These members including the container 201 and the portions disposed therein (the partition wall 204, the hanging walls 217, the table 222) are all preferably made of a metal excellent in corrosion resistance, for example, stainless steel. A tray 240 may be disposed below an outlet of the pipe 226 located in the sterilization chamber 12 to catch liquid components contained in the sterilization gas.

According to the sterilization gas supply device 20 configured in this way, the vaporization unit 23 is placed in a room temperature environment (e.g., 27 degrees C.), and the inside of the vaporization chamber 205 is set to a negative pressure, so that the main component (e.g., hydrogen peroxide) of the sterilant sprayed from the injection port 221 of the nozzle 220 to the first room 206 is mostly vaporized. However, components of relatively high-boiling catalysts (e.g., phosphoric acid and sulfuric acid) contained in the sterilant collide with the sloped upper surface 223 of the table 222 disposed below the nozzle injection port 221 and then flow down along the inclined upper surface 223 before being collected in the liquid reservoir part 224.

On the other hand, the vaporized sterilization gas moves from the first room 206 to the second room 207 through a narrow passage made up of the gaps 210, 215, 216. The sterilization gas enters the sterilization chamber 12 from the second room 207 through the pipe 226.

Since an upper end of the pipe 226 is projected upward from a bottom surface of the container main body 202 in the embodiment as shown in FIG. 6, droplets of the sterilant entering the second room 207 are collected on the bottom of the second room 207, so that very little or almost no droplet enters the sterilization chamber 12 through the pipe 226. Since the passage connecting the first room 206 and the second room 207 is made up of the gaps 210, 215, 216 having a small thickness and a wide width, the sterilization gas moving from the first room 206 to the second room 207 comes into contact with wall surfaces having large areas (the partition wall 204, the hanging walls 213, 214, and the lid lower surface 209). Therefore, the liquid components (particularly, phosphoric acid and sulfuric acid having high boiling points) contained in the sterilization gas are captured by the contact with these wall surfaces and are not carried to the sterilization chamber 12.

3. Test 1

(1) Test Method

A sterilization efficiency of the sterilization device according to the embodiment of the present invention was evaluated by tests (Comparative Example, Examples 1, 2). A test piece used for each of the tests was a tube made of polytetrafluoroethylene (PTFE) having an inner diameter of 1 mm and a length of 1000 mm. One end of the tube was opened, and the other end was closed by applying a biological indicator.

COMPARATIVE EXAMPLE

Figure 7:
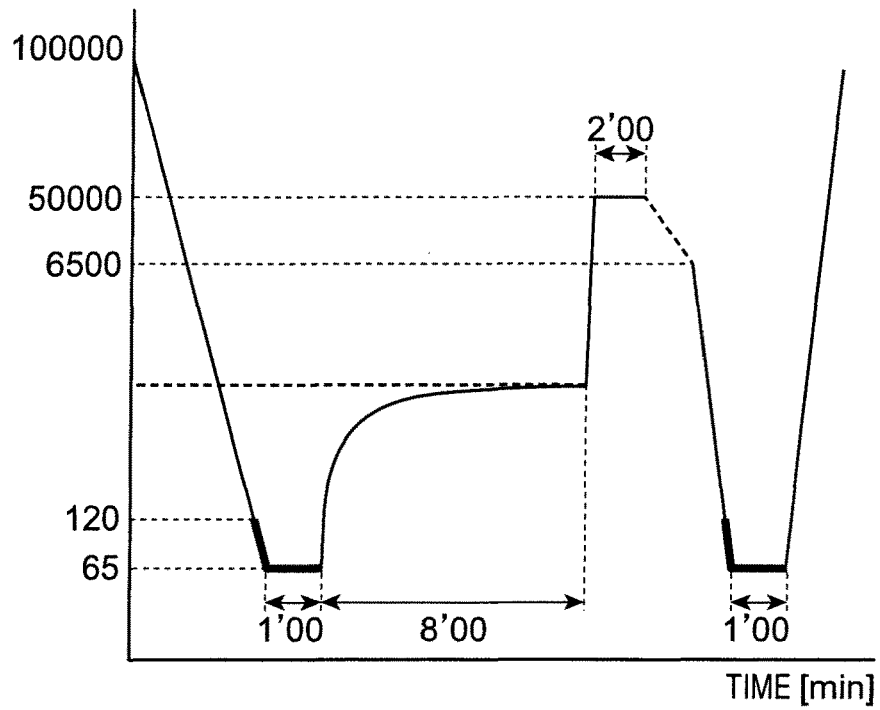
FIG. 7 is a diagram showing a relationship between pressure and time of the sterilization chamber in Comparative Example.

In Comparative Example, the sterilization process shown in FIG. 7 was performed for 20 sterilization objects placed in the sterilization chamber. This sterilization process includes a process of depressurizing the sterilization chamber from the atmospheric pressure to 65 pascals, a process of maintaining the pressure in the sterilization chamber after the depressurization at 65 pascals for 1 minute, a process of injecting 6 ml of a peracetic acid formulation into the sterilization chamber at one time and leaving the formulation for 8 minutes, a process of increasing the pressure in the depressurized chamber to 50,000 pascal, a process of maintaining the pressure in the sterilization chamber after the pressure increase at 50,000 pascal for 2 minutes, a process of depressurizing the sterilization chamber to 65 pascal, a process of maintaining the pressure in the sterilization chamber after the depressurization at 65 pascal for 1 minute, and a process of increasing the pressure in the depressurized chamber to the atmospheric pressure. As shown in FIG. 7, plasma was generated in the depressurized chamber at the first and second depressurization steps in a time zone when the pressure in the sterilization chamber decreases from 120 pascals to 65 pascals and a time zone when the depressurized chamber is maintained at 65 pascals.

Example 1

Figure 8:
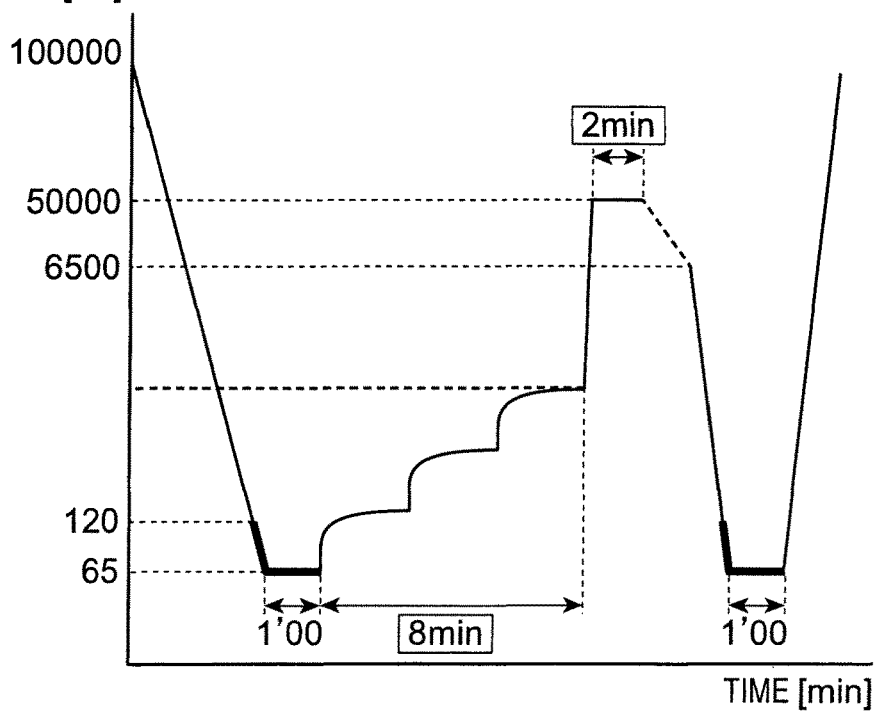
FIG. 8 is a diagram showing a relationship between pressure and time of the sterilization chamber in Example 1.

The sterilization process shown in FIG. 8 was performed for 20 test pieces placed in the sterilization chamber. In this sterilization process, the injection method of the peracetic acid formulation was different from that of the sterilization process of Test 1, and 6 ml of the peracetic acid preparation was injected in three parts. The other conditions are the same as Comparative Example.

Example 2

Figure 9:
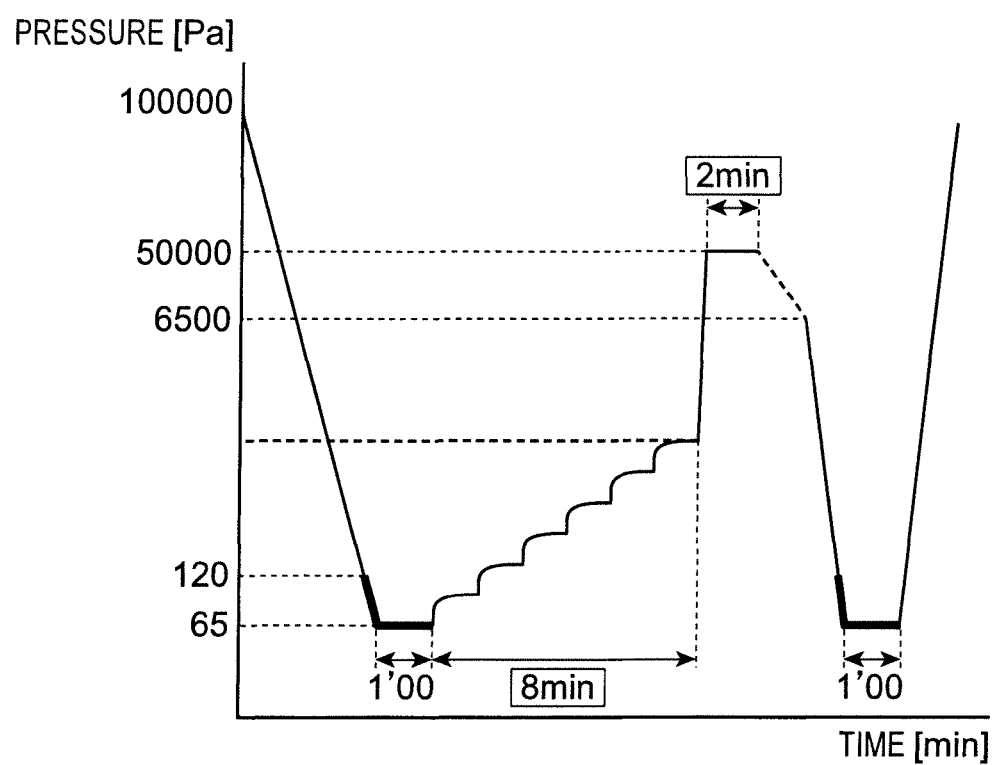
FIG. 9 is a diagram showing a relationship between pressure and time of the sterilization chamber in Example 1.

The sterilization process shown in FIG. 9 was performed for 20 sterilization objects placed in the sterilization chamber. In this sterilization process, the injection process of the peracetic acid formulation was different from the sterilization process of Test 1, and 6 ml of the peracetic acid preparation was injected in six parts. The other conditions are the same as Comparative Example.

After each of the tests was completed, the test pieces ware taken out from the sterilization chamber after sterilization to confirm whether bacteria remained on the biological indicators.

(2) Test Results

The number of test pieces having residual bacteria was "1" for Comparative Example and "0" for Examples 1, 2.

(3) Evaluation

As indicated by the test results, it was confirmed that the sterilization efficiency was further improved by dividedly injecting the sterilant in multiple parts rather than injecting the sterilant into the sterilization chamber at one time.

(4) Corrosion Test

In Examples 1, 2, the tray 240 was disposed at the inlet of the sterilization chamber (directly under the pipe 226) as shown in FIG. 6, and an aluminum foil was laid on the tray 240 to visually check a corrosion mark. As a result, although a slight corrosion mark was confirmed with the naked eye in Example 1, no corrosion mark could be confirmed with the naked eye in Example 2.

5. Test 2

By using the vaporization unit (Example) shown in FIG. 6 and a vaporization unit (Comparative Example) obtained by removing the partition wall, the hanging walls, and the table from the vaporization unit shown in FIG. 6, 6 ml of the peracetic acid preparation was injected in two parts; a second injection of the sterilant was performed after 4 minutes from the first injection of the sterilant; and the pressure in the sterilization chamber was increased to 50,000 pascals after 4 minutes from the second injection of the sterilant. The other conditions are the same as Test 1.

As a result of the test, a large corrosion mark was confirmed with the naked eye on the aluminum foil placed in the tray in Comparative Example. In contrast, no corrosion mark could be confirmed with the naked eye in Example.

6. Other Embodiments

Although the embodiments of the sterilization method and the sterilization device have been described above, the sterilization method and the sterilization device of the present invention can variously be modified. For example, when the sterilant is dividedly injected in the embodiment described above, the timer t2 is started after a predetermined amount (e.g., 1 milliliter) of the sterilant is injected, and the expiration of the timer t2 is waited before starting the next injection of the sterilant; however, the injection timing of the sterilant may be determined by management according to conditions other than the time (pressure increase amount, temporal change rate of pressure).

Figure 10:
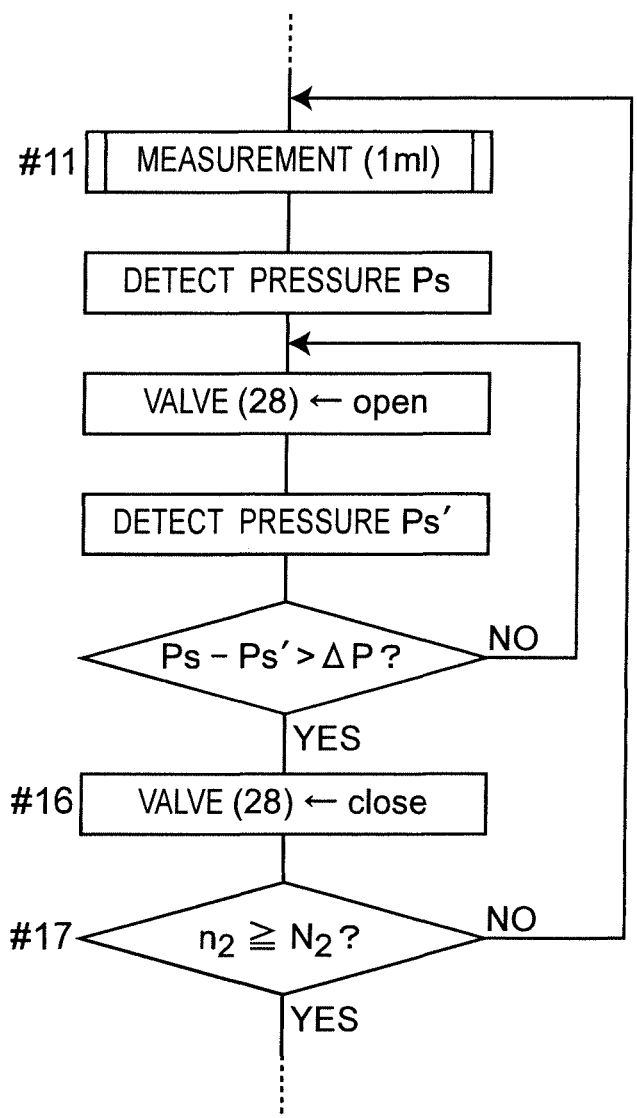
FIG. 10 is a portion of a flowchart showing another form of the present invention.
Figure 11:
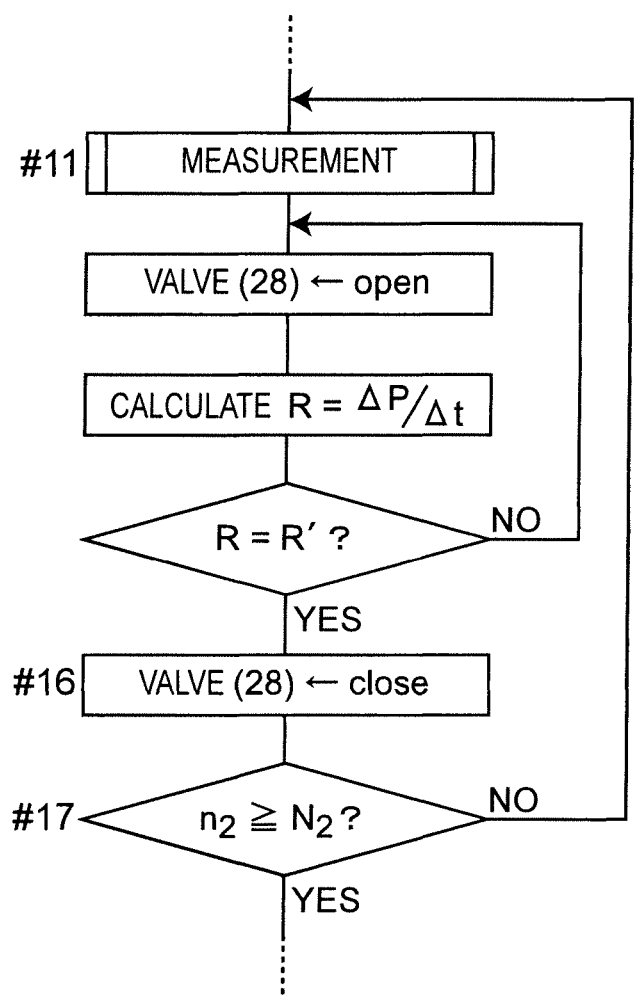
FIG. 11 is a portion of a flowchart showing another form of the present invention.

For example, as shown in FIG. 10, when the measurement is completed, a pressure Ps in the sterilization chamber 12 before opening the valve 28 and a pressure Ps' in the sterilization chamber 12 after opening the valve 28 may be detected, and the valve 28 may be closed when a pressure difference Ps–Ps' exceeds a predetermined amount ΔP. Alternatively, as shown in FIG. 11, when the measurement is completed, the valve 28 is opened, and the valve 28 may be closed when a temporal change rate ($R=\Delta P/\Delta t$) of the pressure in the sterilization chamber 12 reaches a predetermined reference value R'.

In the description, it is described that the vacuum pump 31 is driven when the sterilization chamber 12 is depressurized; however, the vacuum pump 31 activated in the preparation process may be maintained in an operating state during the subsequent process, and the valve 33 may be opened and closed in this state to introduce vacuum into the sterilization chamber 12.

EXPLANATIONS OF LETTERS OR NUMERALS

1: sterilization device
2: sterilization object
10: housing
11: outer container
12: sterilization chamber
20: sterilization gas supply device
21: storage unit
22: measurement unit (measurement chamber)
23: vaporization unit (vaporization chamber)
24: passage (sterilant supply passage)
25: passage (sterilant supply passage)
26: passage (sterilization gas supply passage)
27: valve
28: valve
30: vacuum device
31: vacuum pump
32: passage (exhaust passage)
33: valve
40: ventilation device
41: passage (ventilation passage)
42: valve
50: pressure detector
60: control device
70: plasma generation device
71: inner container
72: room (sterilization chamber)
73: high frequency power source
74: circuit
75: insulation sleeve
201: container
202: container main body
203: lid
204: partition wall
205: internal space (vaporization chamber)
206: first room
207: second room
208: upper end surface
209: lid lower surface
210: gap
211, 212: wall surface
213, 214: hanging wall
215, 216: gap
217: lid portion
220: nozzle
221: injection port
222: sloped table
223: upper surface
224: liquid reservoir part
225: bottom portion
226: pipe

The invention claimed is:

1. A sterilization device comprising:
   a sterilization chamber;
   a vaporization chamber;
   a wall partitioning the vaporization chamber into a first room and a second room;
   a first passage connecting the first room and the second room;
   a table disposed in the first room, the table having an inclined upper surface;
   a nozzle disposed above the table and directed toward the table and configured to spray a sterilant from above toward the table such that liquid components contained in the sterilant collide with the upper surface and then flow along the inclined upper surface;
   a liquid reservoir formed in the first room beside the table and configured to collect the liquid components that flowed down from the table, the liquid reservoir being configured to prevent the collected liquid components from flowing into the second room by gravity;
   a second passage connecting the second room and the sterilization chamber; and
   a vacuum device configured to depressurize the sterilization chamber and the first room and the second room of the vaporization chamber through the first passage and the second passage, wherein
   the first passage is made up of a gap having a thickness and a width, and a length, wherein a thickness of the gap is smaller than a width of the gap, and a length of the gap is longer than the thickness of the gap.

2. The sterilization device according to claim 1, wherein
   the wall includes a partition wall rising from a bottom of the vaporization chamber, and wherein
   the sterilization device includes a second gap formed between an upper end surface of the partition wall and a ceiling surface of the vaporization chamber, wherein a thickness of the second gap is smaller than a width of the second gap.

3. The sterilization device according to claim 2, wherein a tray is disposed below an end portion of the second passage connected to the sterilization chamber.

4. The sterilization device according to claim 1, wherein
   the wall includes a first wall rising from a bottom of the vaporization chamber and a second wall hanging down from a ceiling of the vaporization chamber, and wherein
   the gap is formed between the first wall and the second wall.

5. The sterilization device according to claim 4, wherein a tray is disposed below an end portion of the second passage connected to the sterilization chamber.

6. The sterilization device according to claim 1, wherein a tray is disposed below an end portion of the second passage connected to the sterilization chamber.

7. The sterilization device according to claim 1, when fluid passes from the first room to the second room it flows in the length direction of the gap.

8. The sterilization device according to claim 1, further comprising a second reservoir in the second room for collecting sterilant that condenses in the first passage, the second reservoir being configured to prevent the condensed sterilant from flowing into the first room by gravity.

9. A sterilization device comprising:
   a sterilization gas supply means having a sterilant spray nozzle;
   a vaporization unit;
   a sterilization chamber; and
   a vacuum device introducing a vacuum into the sterilization chamber;
   (a) the sterilization gas supply means comprising:
      a container having a container body including an upper opening and an upper lid closing the upper opening of the container body, the container body and the upper lid defining a vaporization chamber inside the container;
      a partition wall extending upward from a bottom wall of the container body toward the upper lid to divide the vaporization chamber into a first room and a second room and form a first passage made of a gap defined between the partition wall and the upper lid, the first passage communicating between the first room and the second room;
      a table positioned in the first room, wherein an upper surface of the table is sloped, and a liquid reservoir is formed in the first room beside the table; and
      a second passage communicating between the second room and the sterilization chamber;
   (b) the sterilization gas supply means having a sterilant spray nozzle coupled to a portion of the upper lid defining a part of the first room and faced toward the table such that a sterilant from the sterilant spray nozzle is sprayed toward the table, causing liquid components contained in the sterilant to collide with the table and then flow down into the liquid reservoir to be collected in the liquid reservoir while a vaporized component contained in the sterilant is guided, by means of the vacuum, from the first room through the first passage, the second room and the second passage into the sterilization chamber, the liquid reservoir being configured to prevent the collected liquid components from flowing into the second room by gravity.

10. The sterilization device according to claim 9, further comprising a second reservoir in the second room for collecting sterilant that condenses in the first passage, the second reservoir being configured to prevent the condensed sterilant from flowing into the first room by gravity.

* * * * *